(12) United States Patent
Lyoussi et al.

(10) Patent No.: US 7,683,329 B2
(45) Date of Patent: Mar. 23, 2010

(54) METHOD AND SYSTEM FOR DETERMINING THE DENSITY AND DIMENSIONAL CHARACTERISTICS OF AN OBJECT AND APPLICATION TO CHECKING OF NUCLEAR FUEL PELLETS DURING MANUFACTURING

(75) Inventors: Abdallah Lyoussi, Manosque (FR); Emmanuel Payan, Manosque (FR)

(73) Assignees: Commissariat a l'Energie Atomique (FR); Compagnie Generale des Matieres Nucleaires (FR)

( * ) Notice: Subject to any disclaimer, the term of this patent is extended or adjusted under 35 U.S.C. 154(b) by 244 days.

(21) Appl. No.: 10/594,834

(22) PCT Filed: Apr. 6, 2005

(86) PCT No.: PCT/FR2005/000838

§ 371 (c)(1),
(2), (4) Date: Apr. 27, 2007

(87) PCT Pub. No.: WO2005/100952

PCT Pub. Date: Oct. 27, 2005

(65) Prior Publication Data

US 2007/0295897 A1   Dec. 27, 2007

(51) Int. Cl.
*G01B 15/00* (2006.01)
(52) U.S. Cl. .................. 250/360.1; 250/358.1
(58) Field of Classification Search ............. 250/358.1, 250/359.1, 360.1, 492.1
See application file for complete search history.

(56) References Cited

U.S. PATENT DOCUMENTS 4,193,502 A   3/1980  Marmo 6,151,379 A   11/2000  Kullenberg et al.

FOREIGN PATENT DOCUMENTS

| DE | 197 10 835 A1 | 3/1997 |
| DE | 19710835 | 9/1998 |
| FR | 2 798 463 | 9/1999 |
| FR | 2798463 | 3/2001 |

OTHER PUBLICATIONS

Experimental Evaluation Of A Laboratory Twin-Probe Nuclear Gage For Specimen Density Measurement, pp. 59-65 from Journal Of Testing And Evaluation (Jan. 20, 1992), No. 1, Philadelphia, PA.
Above references cited in European Search Report which was filed with the U.S. application on Sep. 28, 2006, with English abstracts of the German and French references having been filed in applicants' IDS dated Dec. 18, 2006.

*Primary Examiner*—David P Porta
*Assistant Examiner*—Mark R Gaworecki
(74) *Attorney, Agent, or Firm*—Baker & Hostetler, LLP

(57) ABSTRACT

The system for automatic determination of the density of an object (100) comprises:
  an apparatus (2) to determine a significant dimension (x) of said object (100),
  an apparatus (30) to determine the intensity (I) of a photon beam attenuated by passing through said object (100),
  an acquisition, processing and analysis apparatus (200),
  means (70, 72, 80, 82, 84, 86, 88) of transporting the object (100),
  first means (74, 76, 78) of adjusting the position of the object (100),
  second means (90, 92, 94, 96, 98) of adjusting the position of the object (100).

The method for using the system described above includes steps to calibrate components of apparatuses 2 and 30, and steps to actually determine the significant dimension of objects (100), that are done on each object (100) in said set of objects.

30 Claims, 12 Drawing Sheets

PRELIMINARY CALIBRATIONS

Step 1
calibrate the position of the two infrared assemblies of the apparatus to determine the significant dimension of the object Step 2
calibrate the position of the irradiation support of the apparatus to determine the intensity of the photon beam attenuated by passing through the object Step 3
calibrate the measurement of the source - detector assembly of the apparatus to determine the intensity of the photon beam attenuated by passing through the object.

FIGURE 9A

ACTUAL DETERMINATION OF THE
RELATIVE VARIATION OF THE DENSITY

Step 4
determine the significant dimension of the object to be tested

Step 5
transport the object to the irradiation support

Step 6
adjust the position of the object by adjusting the position
of the irradiation support with respect to a source and an
associated detector Step 7
determine the attenuated intensity of the photon beam
transmitted through the object Step 8
acquisition, processing and analysis of the spectrum obtained Step 9
determine the relative variation of the density of the object
with respect to the density of one or several objects with
standard density Step 10
return transport of the object to its location on the turntable.

FIGURE 9B

| Step 3 |
|---| a) measure the photon intensity Iemas attenuated by passing through a standard density object emas used as a reference b) calculate the mass attenuation coefficient μm of the standard density object using the following relation:

$$\rho_{emas} = -\frac{1}{\mu_m x_{emas}} L_n \frac{I_{emas}}{I_o}$$

FIGURE 12

Step 9 automated calculation of the relative variation $\frac{\Delta \rho}{\rho}$ of the density of the object 100 with respect to the density of one or several standard density object(s) emas using the following relation:

$$\frac{\Delta \rho}{\rho} = \frac{X_{emas}}{X}\left[1 - \frac{L_n \frac{I}{I_{emas}}}{\mu_m \rho_{emas} X_{emas}}\right]$$

FIGURE 14

METHOD AND SYSTEM FOR DETERMINING THE DENSITY AND DIMENSIONAL CHARACTERISTICS OF AN OBJECT AND APPLICATION TO CHECKING OF NUCLEAR FUEL PELLETS DURING MANUFACTURING

TECHNICAL DOMAIN

This invention relates to the domain of non-destructive analysis techniques.

More specifically, the invention is applicable to a method and a system for automatic determination of the density of objects by straight line photon attenuation and their dimensional characteristics.

One of its applications is the inspection and monitoring of the correct operation of object manufacturing and machining units, for example such as nuclear fuel pellets such as UOX and/or MOX, and is used particularly to monitor reproducibility of manufacturing of said objects, related to their density.

It can also be used to determine axial and radial density gradients, thus acting as a very precise computed tomography (CT) scanner.

STATE OF PRIOR ART

Non-destructive active nuclear methods for determination of the density have already been produced, particularly to determine the density of geological samples. In the reference document Been, K., "*Non-destructive Soil Bulk density Measurement by X-ray Attenuation*" *Geotechnical Testing Journal, GTJODJ,* Vol. 4, No. 4, December 1981, pp 169-176, the author proposes a samples density measurement by straight line photon attenuation using X-ray tubes, without attempting to precisely determine the dimension of the samples concerned. In reference documents Tan, S.-A and Fwa T.-F., "*Non-destructive Density Measurements of Cylindrical Specimens by Gamma-Ray Attenuation*", *Journal of Testing Evaluation, JTEVA,* Vol. 19, No. 2, March 1991, pp. 155-160, and Tan, S.-A and Fwa, T.-F "*Density Measurements of Cylindrical Specimens within a Mold by Gamma-Rays*", *Journal of Testing Evaluation, JTEVA,* vol. 21, No. 4, July 1993, pp. 296-301, the authors propose a measurement of the density of geological samples by straight line photon attenuation using gamma radiation. They have identified and demonstrated the influence of geometric parameters of samples on the precision of the density measurement, but they did not propose a solution to precisely determine said geometric parameters.

Note that although the documents mentioned above relate to the density of samples, the objective is actually to determine the mass per unit volume of said objects, and the term "density" is used instead of "mass per unit volume" to simplify the description.

PRESENTATION OF THE INVENTION

The purpose of this invention is to determine the density of objects belonging to a given set of objects, by determining the variation of the density of each of said objects with respect to the known density of at least one of said objects used as a reference or a standard.

This determination of the density of said objects is made using a non-destructive nuclear technique, consisting of irradiation by gamma photons and using a gamma spectrometry apparatus to determine the intensity of the gamma photon beam.

Determination of the density of said objects requires prior determination of at least one significant dimension of the objects.

Unlike the methods described in prior art mentioned above, the invention takes account of the influence of geometric parameters by very precisely measuring at least one significant dimension of the objects for which the density is to be determined, and using this measured significant dimension to determine the density of the tested objects. Said significant dimension may be a width or a diameter and corresponds to the effective dimension through which the gamma photon beam passes.

The method for determination of the significant dimension of the object forms part of the method to determine the density of said object. It uses an infrared radiation apparatus for measuring the dimension.

Remember briefly that the physical principle for determination of the density of an object by photon attenuation consists of irradiating the object with a query beam composed of monochromatic photons with energy E. The intensity of the photon beam is attenuated more or less as a function of the density of the object through which it passes, the thickness of the material through which it passes, and the elementary chemical composition of the object through which it passes. This intensity is given by the following equation:

$$I = I_o \exp(-\mu_m \rho X)$$

where:

I is the attenuated intensity of the photon beam, in photons$^{-1}$, $I_o$ is the non-attenuated intensity of the photon beam with energy E, in photons$^{-1}$, $\mu_m$ is the mass attenuation coefficient of the photon with energy E in the object, in cm$^2 \cdot$g$^{-1}$, $\rho$ is the density of the object to be tested, in g·cm$^{-3}$, X is the thickness of the material through which the photon beam passes, or the significant dimension of the object, in cm.

The expression for the density of the object is deduced directly by:

$$\rho = \frac{\text{Ln}\left[\frac{I_o}{I}\right]}{\mu_m X}.$$

Thus, if the intensities transmitted with and without insertion of the object to be tested (I and $I_o$ respectively), the mass attenuation coefficient $\mu_m$ and the significant dimension x of the object actually passed through are known, the density $\rho$ of said object can be determined.

This invention proposes to determine the thickness of material x of the object through which the photon beam passes and the transmitted intensity I of the photon beam at energy level E, and to use these values to calculate the relative variation of the density $\rho$ of this object with respect to the density of at least one reference standard object. One characteristic of the invention lies in the fact that these determinations of the material thickness (significant dimension of the object) and the intensity of the photon beam are made with a precision of about one micron.

The relative variation of the density $\rho$ of the object to be tested is obtained using the following expression:

$$\frac{\Delta\rho}{\rho} = \frac{\rho - \rho_e}{\rho} = \frac{x_e}{x}\left[1 = \frac{L_n \frac{I}{I_e}}{\mu_m \rho_e x_e}\right]$$

where $\rho_e$ is the known density of the object used as a density standard, and $x_e$ is the significant dimension passed through in the object with standard density.

The mass attenuation coefficient $\mu_m$ that depends on the chemical composition of the object, is determined from one or several certified and perfectly known standard objects, with the same chemical composition as the object to be tested. It is determined during one step that will be described in the following, for calibration of the apparatus to determine the intensity of the photon beam, attenuated by passing through the standard object.

When the object to be tested has a circular section, the significant dimension passed through corresponds to its diameter. When the object to be tested is parallelepiped in shape, the significant dimension passed through is a width of the object.

In the rest of the description, the following notations will be used when it is required to distinguish an object i among the set of objects 100 and/or a standard object e among the set of objects 100:

the index emas is representative of magnitudes relative to an object with standard density, for example its significant dimension $x_{emas}$, the index edim is representative of magnitudes relative to an object with standard dimension, for example its significant dimension $x_{edim}$.

According to a first aspect of the invention, the system for automatic determination of the density of an object belonging to a set of objects comprises:

an apparatus to determine a significant dimension of said object, an apparatus to determine the intensity of a photon beam attenuated by passing through said object, an acquisition, processing and analysis apparatus, means of transporting the object to the apparatus for determining its significant dimension and towards the apparatus for determining the attenuated intensity of the photon beam, first means of adjusting the position of the object relative to the apparatus for determining the significant dimension, second means of adjusting the position of the object relative to the apparatus for determining the attenuated photon intensity, said first and second adjustment means being capable of moving the object with a precision of the order of one micron with respect to a support plate on which the elements making up the system are installed, and the position of the object relative to the apparatus for determining the attenuated intensity being adjusted as a function of the significant dimension of said object.

Preferably, the apparatus for determining a significant dimension of the object is a measurement apparatus using infrared radiation.

Preferably, the apparatus to determine the intensity of a photon beam attenuated by the crossing through the object is a gamma spectrometry determination apparatus, that comprises:

an assembly composed of a source and a collimator, an assembly composed of a detector and a collimator, a gamma photon acquisition and counting system.

The invention uses transport means and means of adjusting the position of each tested object with respect to the apparatus for determining the significant dimension of the object and/or with respect to the apparatus for determining the attenuated intensity, said position adjustment means being capable of providing a precision of the order of one micron.

According to a second aspect, the invention relates to a process for using the system for automatic determination of the density of an object (100) belonging to a set of objects, and includes the following calibration steps:

a step 1 to calibrate the position of two infrared assemblies in the apparatus to determine the significant dimension of objects, a step 2 to calibrate the position of an irradiation support of the gamma spectrometry apparatus used to determine the intensity of the photon beam attenuated by passing through objects, a step 3 to calibrate the measurement of a source-detector assembly of the gamma spectrometry apparatus used to determine the intensity of the photon beam attenuated by passing through objects, and it includes steps to actually determine the significant dimension of objects, which are done on each object in said set of objects.

According to the invention, the actual determination steps include:

a step 4 to determine the significant dimension of the object to be tested, a step 5 to transport the object to an irradiation support, a step 6 to adjust the position of the object by adjusting the position of the irradiation support with respect to a source and an associated detector, a step 7 to determine the attenuated intensity of the photon beam transmitted through the object, a step 8 for acquisition, processing and analysis of the spectrum obtained, a step 9 for determination of the relative variation $$\frac{\Delta\rho}{\rho}$$

of the density of the object with respect to the density of one or several object(s) with standard density, a transport step 10 to return the object to its position on the turntable.

The methods and devices according to the invention have the advantage that they are fast, precise, automatic or can be automated, and are easy to use.

One advantage of the invention lies in the fact that it associates straight line photon attenuation with micrometric metrology so as to overcome uncertainties related to poor knowledge of the thicknesses of objects passed through, and that directly affect the precision with which the density is determined.

In particular, the position of each object relative to the apparatus used to determine the photon intensity attenuated by the crossing through said object is adjusted as a function of a significant dimension of the object, and that had previously been determined by the apparatus used to determine the significant dimension.

BRIEF DESCRIPTION OF THE FIGURES

The invention will be better understood after reading the detailed description of a preferred embodiment given below as a non-limitative example that is illustrated by the appended figures, wherein:

FIGS. 9A and 9B show all steps in the method for determination of the density of objects; FIG. 9A illustrates preliminary calibration steps and FIG. 9B illustrates the actual determination steps;

FIG. 12 illustrates the third step of the method that is a step to calibrate the measurement of the apparatus to determine the attenuated photon intensity;

FIG. 14 illustrates the ninth step of the method that is a step to determine the relative variation of the density of the object with respect to the relative variation of one or several standard objects;

DETAILED PRESENTATION OF ONE PARTICULAR EMBODIMENT

Figure 1:
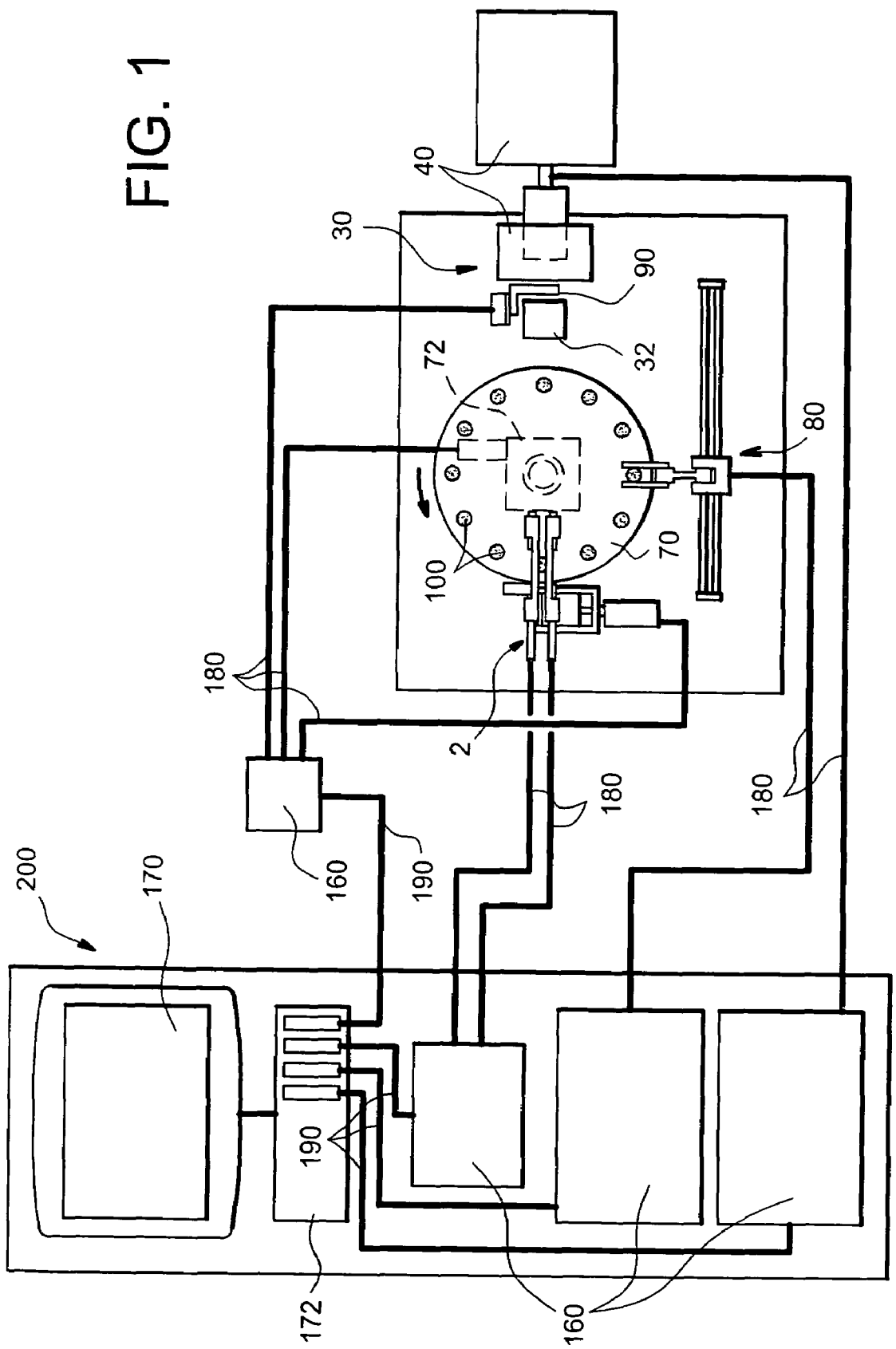
FIG. 1 shows a diagrammatic top view of the general system for determination of the significant dimension and for determination of the density of objects.
Figure 2:
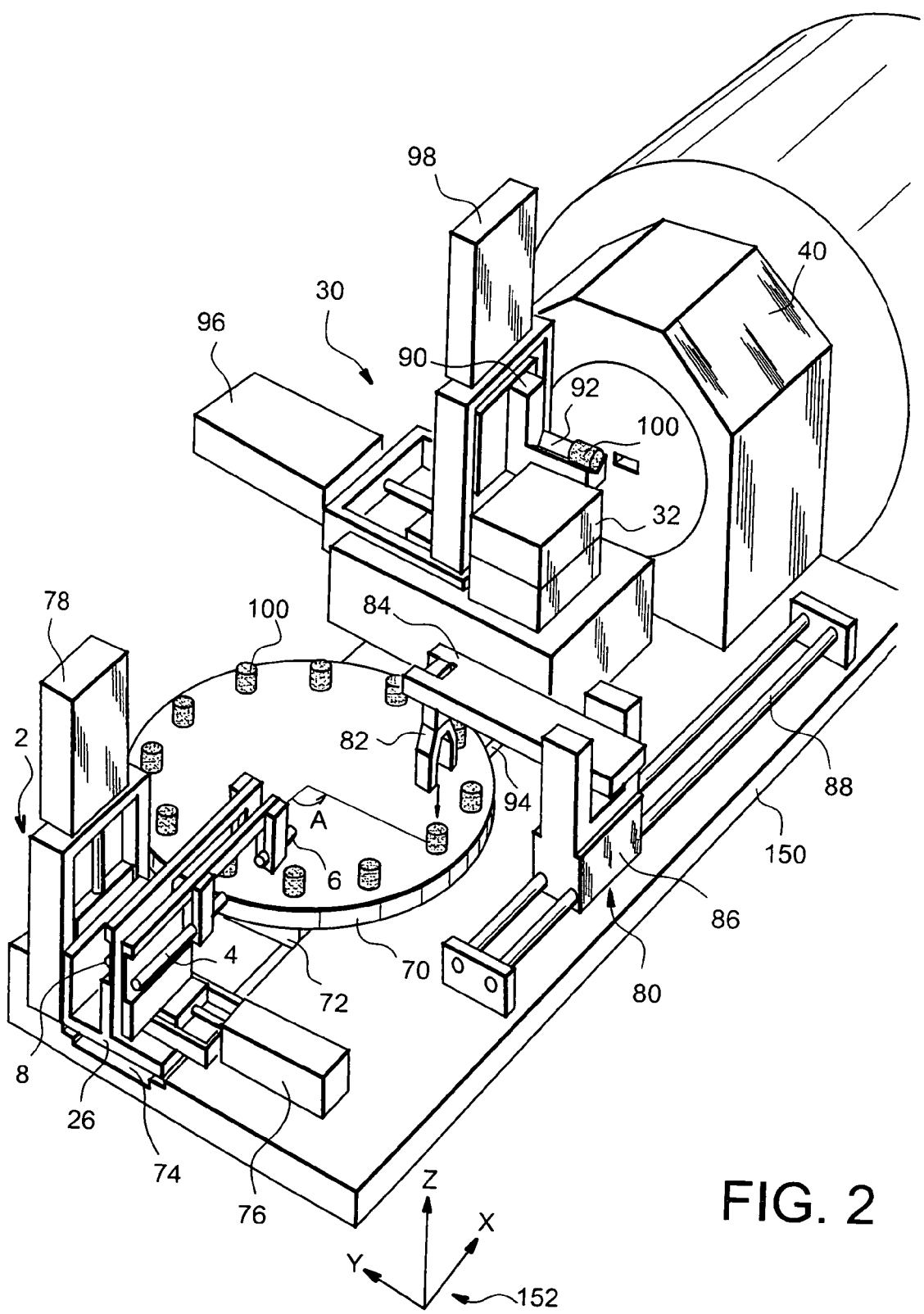
FIG. 2 shows a diagrammatic perspective view of the general system for determination of the significant dimension and for determination of the density of objects.

FIGS. 1 and 2 illustrate a top view and a perspective view respectively of a preferred embodiment of the general system for determination of the density of each object 100 in a set of objects by photon attenuation, by determining the relative variation of this density with respect to the density of at least one of said objects used as a standard density or reference, this density determination making use of the preliminary determination of a significant dimension x of said object 100, and the intensity I of the photon beam that irradiates and passes through said object 100.

The system includes the following components:

an apparatus 2 for determination of the significant dimension of the object 100, an apparatus 30 for determination of the intensity of the photon beam attenuated by passing through the object 100, an acquisition, processing and analysis apparatus 200, transport means 70, 72, 80, 82, 84, 86, 88 and position adjustment means 74, 76, 78, 90, 92, 94, 96, 98 of the object 100 with respect to the dimension determination apparatus 2 with respect to the intensity determination apparatus 30, respectively.

The acquisition, processing and analysis apparatus 200 is shown diagrammatically as a whole in FIG. 1. In particular, it includes a PC type computer 170 on which a dedicated software is installed that runs series of instructions and calculation algorithms used in the automatic method for determination of the density of objects 100 according to the invention.

Figure 3:
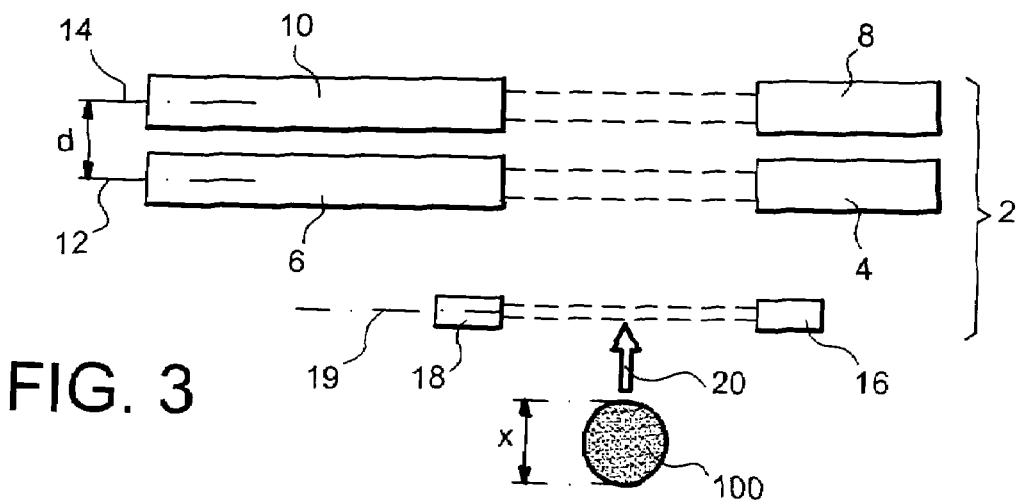
FIGS. 3, 4 and 5 illustrate a diagrammatic top view of the device for determination of a significant dimension of objects by means of infrared radiation, and three phases in the method to determine this significant dimension.
Figure 4:
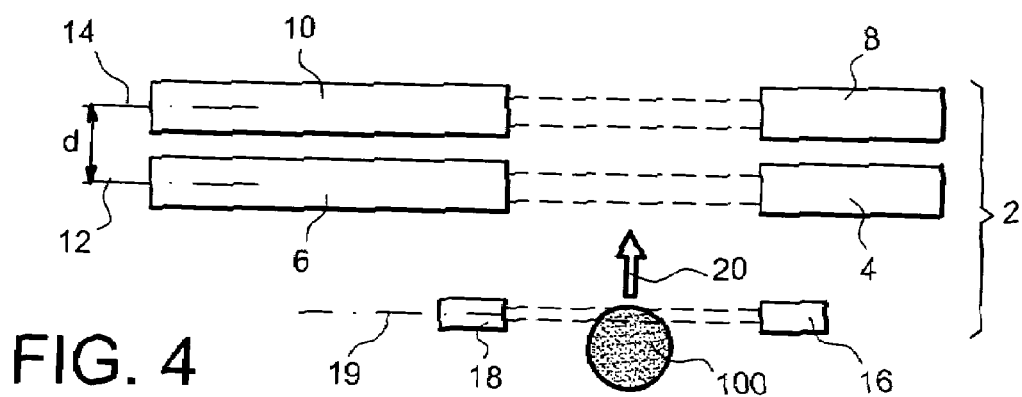
Figure 5:
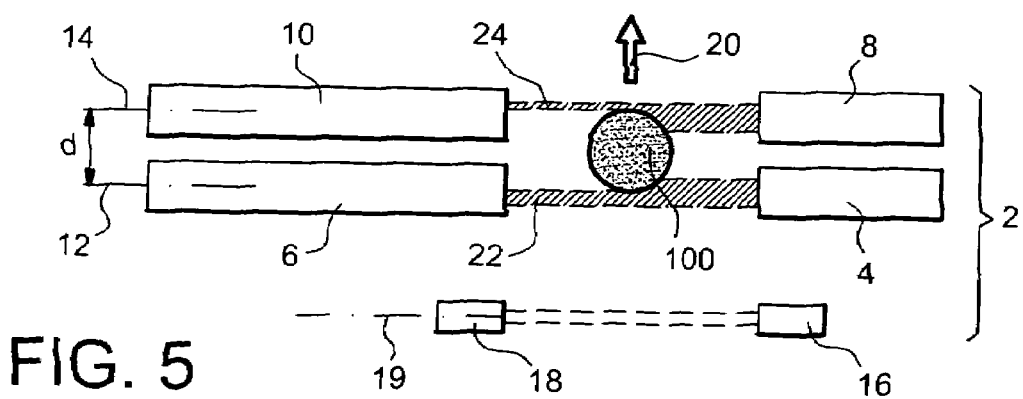

With reference to FIGS. 3, 4 and 5, the infrared radiation apparatus 2 used for determination of a significant dimension x of the object 100 includes:

a first infrared assembly 4, 6 composed of a first infrared emitter 4 and a first infrared receiver 6, a second infrared assembly 8, 10 composed of a second infrared emitter 8 and a second infrared receiver 10.

The two infrared assemblies 4, 6, and 8, 10 are arranged such that the corresponding axes 12, 14 of the infrared radiation beams that they generate are parallel to each other and are separated by a distance d. This distance d fixed by the manufacturer is chosen so as to be of the same order of magnitude as the significant dimension x of objects 100 to be tested. It is adjustable. The infrared beams are oriented in the same direction in the example illustrated, but a different configuration could be envisaged.

The apparatus 2 for determination of the significant dimension x of the object 100 by infrared radiation also includes a third assembly composed of a photoelectric emitter 16 and a photoelectric receiver 18, arranged on the input side of the first infrared assembly 4, 6 with respect to the second infrared assembly 8, 10, the photoelectric beam that it generates having an axis 19. In the example shown, the axis 19 of the photoelectric beam is parallel to the axes 12, 14 of the infrared beams, and is located in the same plane as them. A different configuration could be envisaged.

The apparatus 2 for determination of the significant dimension x of the object 100 by infrared radiation is associated with transport means and/or means of adjusting the position of the object 100 with respect to the three transceiver assemblies 4, 6, 8, 10, 16, 18 that will be described in the following.

During operation, the apparatus 2 for determination of the significant dimension of the object 100 is located in a situation in which the three transceiver assemblies 4, 6, 8, 10, 16, 18 are fixed, and the object 100 is displaced so as to successively intercept the photoelectric beam, then the first infrared beam, then the second infrared beam.

The apparatus 2 is calibrated so as to create a distance d between the axes 12 and 14 of the two infrared radiation beams that are substantially the same as the significant dimension $x_{edim}$ of one or several objects with standard dimension edim. This calibration will be described later. It then follows that during determination of the significant dimension of object 100 (non standard), the object moves relative to the three transceiver assemblies 4, 6, 8, 10, 16, 18 and passes through at least one position in which it still intercepts half of the first infrared beam (FIG. 5, reference 22) and does not yet intercept the entire second infrared beam, leaving a fraction of the second beam (FIG. 5, reference 24) that is not intercepted by the object 100, and that reaches the second receiver 10.

The significant dimension x of the object 100 is deduced from the infrared response RI corresponding to this non intercepted beam fraction. This dimension is obtained by a relation of the following type:

$$x = A_4 \cdot (RI^4) + A_3 \cdot (RI^3) + A_2 \cdot (RI^2) + A_1 \cdot (RI^1) + A_0,$$

where $A_4, A_3, A_2, A_1, A_0$ are coefficients obtained using at least four objects with standard dimension edim, and applying the same relation in which the known significant dimension $x_{edim}$ and the measured infrared response $RI_{edim}$ of each of said objects with standard dimension edim are injected, once for each object with standard dimension.

As shown in FIG. 4, the function of the third assembly 16, 18 is to automatically trigger prior adjustment of the intensity of the two infrared beams 22, 24, when the object 100 intercepts the photoelectric beam generated by this third assembly 16, 18, during the relative displacement along the direction 20. The purpose of this operation is to eliminate the influence of environmental disturbances such as optical lenses getting dirty. It must occur not later than 30 seconds before the measurement operation itself on the object 100.

The precision with which the significant dimension x of the object 100 is determined depends on the precision of the relative displacement of the object 100 with respect to the three transceiver assemblies 4, 6, 8, 10, 16, 18 and therefore on the performances and calibration of the transport and/or position adjustment means, aspects that will be described in more detail later.

Figure 8:
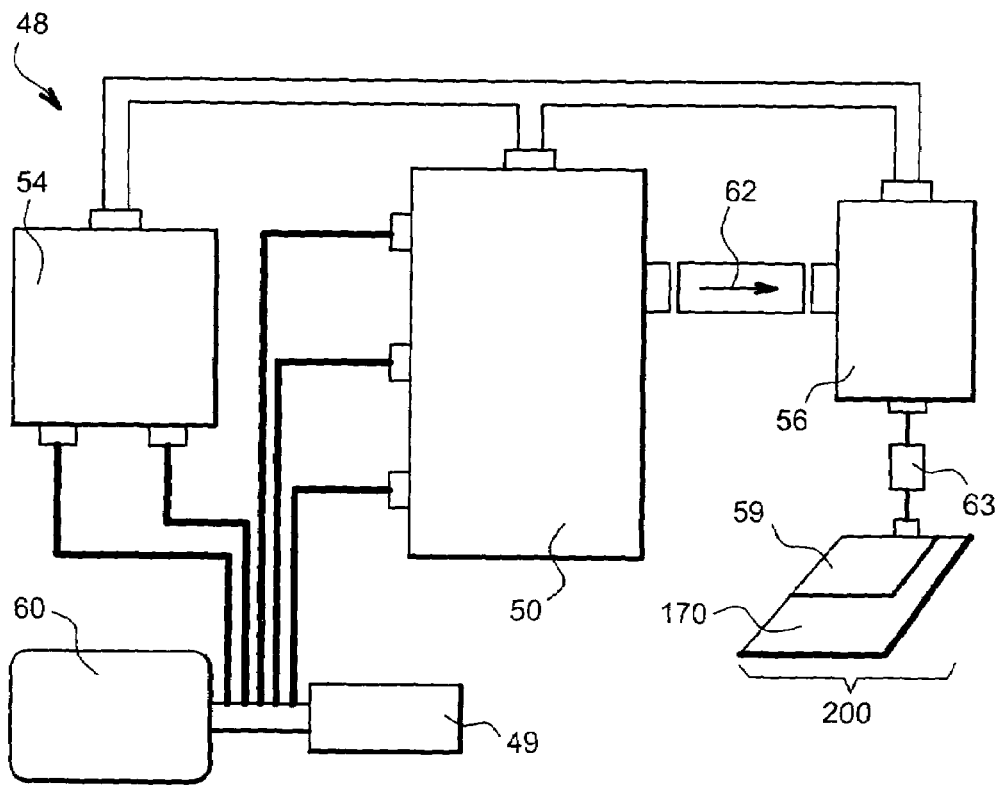
FIG. 8 is a diagrammatic view showing the acquisition and counting system.

According to the invention, the intensity I of the photon beam is determined using a gamma spectrometry apparatus 30 to determine the intensity of the photon beam that irradiates and passes through the objects 100, as shown in FIGS. 1, 2 and 8. This includes:

an assembly formed from a photon irradiation source and a collimator 32, of a type known in itself,
an assembly formed from a detector and a collimator 40, of a type known in itself,
an acquisition and counting system 48, of a type known in itself.

The photon irradiation source will be called the "source" in the following, to simplify the description.

The different components of the determination apparatus 30 are subjected to some constraints related to the required performance for the general system, and the environment in which the system will operate. These constraints, that relate particularly to the source intensity, the source type and the performances of the acquisition and counting system, are as follows:

the intensity of the source must be such that the statistical dispersion of the measurement results is significantly less than the count variation due to a difference in the density of the object to be tested with respect to the density of the reference standard object,
the source energy must enable very good contrast following a minor variation of the density of the object to be tested,
the radioactive half-life of the source must not be too short so that it is restrictive in an industrial environment,
finally, the intensity and the energy of the source must be compatible with processing capabilities of the electronic acquisition and counting system (dead time, stacking, saturation, etc.).

In the preferred embodiment, the source is made of $^{133}$Ba with an activity of at least 10 mCi. To avoid the effects of dead time and/or saturation, it is preferable to use a source with an activity not exceeding 150 mCi. The measurement duration is inversely proportional to the activity of the source.

Figure 6:
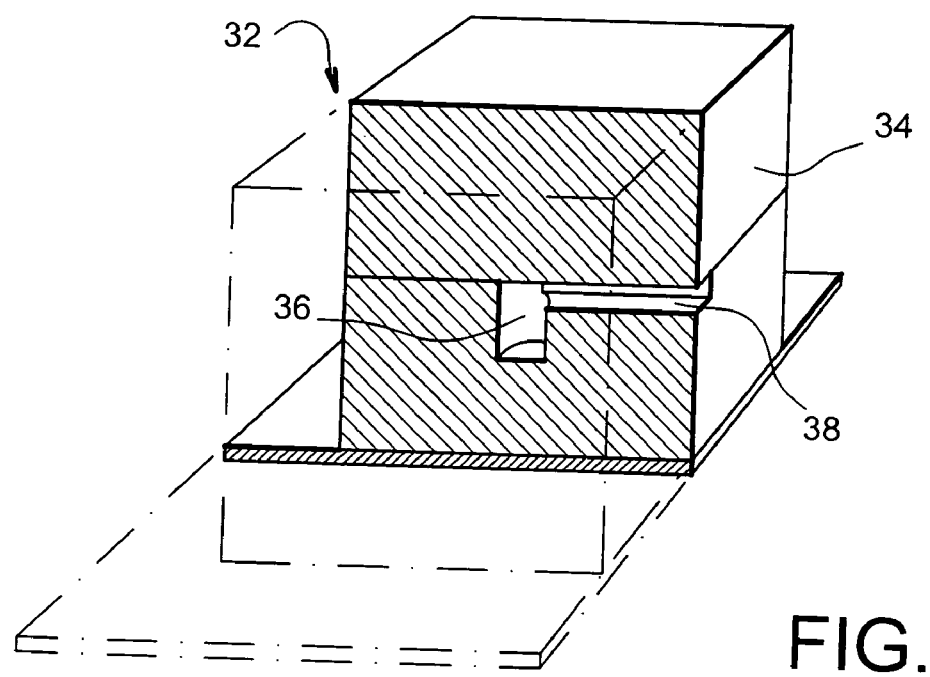
FIG. 6 shows a perspective and sectional view of the collimator in the photon irradiation source.

FIG. 6 illustrates an example embodiment of the collimator 32 of the source-collimator assembly, compatible with these different constraints. It includes a protection formwork 34 to protect persons working close to the source that delimits a cavity 36 in which the source is housed. The gamma photon beam is guided by a collimation slit 38.

According to the example embodiment illustrated, the collimator 32 of the source is made of lead and its outside dimensions are 60 mm in height, 60 mm in length and 60 mm in width. The source is a $^{133}$Ba source with an activity of 10 mCi, housed in a cavity 36 with a diameter of 6.1 mm and a height of 9.5 mm. The collimation slit 38 is 30 mm long, 6 mm wide and 4 mm high.

Figure 7:
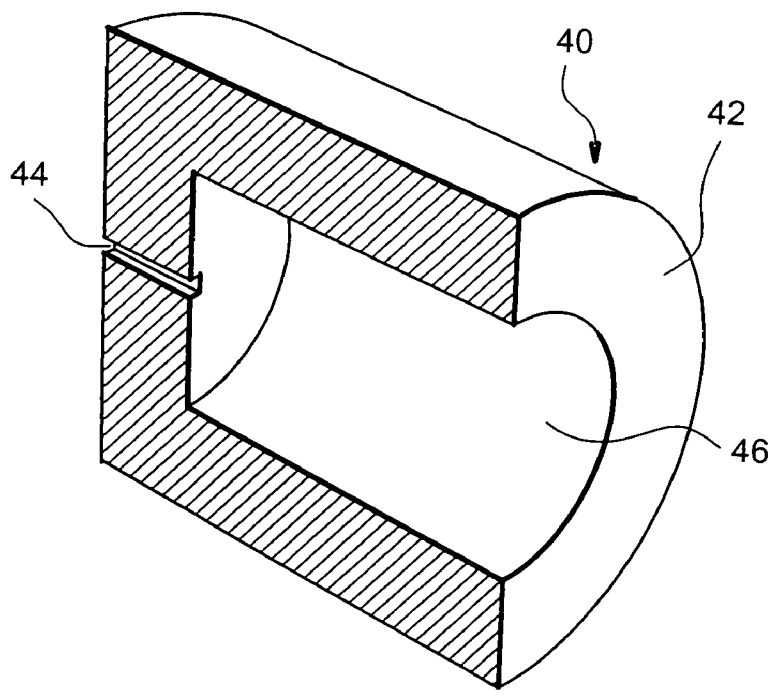
FIG. 7 shows a perspective and sectional view of the collimator in the gamma photon detector.

FIG. 7 shows an example embodiment of the collimator 40 in the detector-collimator assembly. It includes a protection formwork 42 so that the gamma rays output from the source and emitted outside the collimation slit 38 are not detected by the detector 49, a collimation slit 44 and a cavity 46 to house the detector 49 delimited by the protection formwork 42.

In the example embodiment shown, the collimator 40 of the detector 49 is made of lead and its outside dimensions are 140 mm in diameter and 120 mm in length, and its inside dimensions are 80 mm in diameter and 200 mm long. The collimation slit is 4 mm high, 6 mm wide and 30 mm long.

The lead in the protection formwork 42 may be replaced by tungsten that attenuates gamma rays more than lead, which has the advantage that it reduces the thickness of the protection formwork 42, but the disadvantage of tungsten is that its price is higher than the price of lead.

In the following and to simplify the description, the source-collimator assembly will simply be called the "source" and will be marked as reference 32, and the detector-collimator assembly will simply be called the "detector" and will be marked as reference 40.

The source-detector distance is chosen appropriately.

According to the preferred embodiment, the acquisition and counting system 48 shown in FIG. 8 includes:

a detector 49 in the form of a high purity germanium Ge diode [HP] with a preamplifier,
a digital signal processor (DSP) 50,
a high voltage module 54,
an acquisition and interface network module (AIM) 56,
a PC type data acquisition computer 170 (FIG. 1).

Optionally, the acquisition and counting system includes a cryostat 60 composed of a liquid nitrogen tank that keeps the cold finger of the Ge diode [HP] at a constant temperature, which has the advantage of minimising the Doppler effect and giving very good signal resolution, the measurements not being disturbed by heating of the detector 49.

The preamplifier is preferably incorporated into the Ge diode [HP], which has the advantage of minimising the capacitance effect due to the electrical cable and reduces electronic background noise. It also filters and shapes the signal.

The signal is then digitised using the signal processing module 50 and is then put into memory.

The set of information obtained makes up the gamma spectrum, in other words the histogram sorting the number of pulses into different channels as a function of their energy.

Data are transferred (arrow 62) between the signal processing module 50 and the computer 170 of the acquisition, processing and analysis apparatus 200, through the acquisition and interface network module 56, a transceiver 63, a network card 59. In the example illustrated, the acquisition, processing and analysis apparatus 200 and the acquisition and counting system 48 use the same computer 170, but a configuration with two separate computers could be envisaged.

This acquisition and counting system 48 is particularly suitable for high counting rates.

Furthermore, another constraint for use of the gamma spectrometry apparatus 30 for determination of the intensity of the photon beam that irradiates the objects 100 relates to the count time of the acquisition and counting system 48, that must respect manufacturing rates of objects 100 to be tested.

According to the invention, the count time can be a system input data, or the result of a calculation output by the following theoretical relation:

$$t = \frac{\alpha^2}{A(t) \cdot \frac{S}{4\pi D^2} \cdot \varepsilon \cdot \frac{\Sigma}{P} \cdot R_0 \cdot \left(R_o^{\beta_{SEC}} - 1\right)^2}$$

with an approximation by which the solid angle is equal to $4\pi D^2$.

where:

A(t) is the activity of the source in Bq,

D is the distance between the source and a collimation window, in mm,

S is the surface area of the detector collimation window, in mm$^2$,

α is the width of the confidence interval for the case in which counting follows a Poisson's distribution, ε is the total absorption efficiency of the photon detector, I is the intensity of the photon beam at energy E, attenuated by crossing through the object, in γ·s$^{-1}$, I$_o$ is the non-attenuated intensity of the photon beam at energy E, in γ·s$^{-1}$.

$$R_o = \frac{I}{I_o}$$

is the transmission coefficient of the object through which monochromatic photons output by the source pass, Σ is the total number of hits recorded in the measured spectrum, in hits, P is the total number of hits contained in the energy peak E, $$\beta_{SEC} = \frac{\beta}{10}$$

is a value of β assigned by a safety factor equal to 10, where $$\beta = \frac{\Delta \rho}{\rho},$$

and where ρ is the density of the object.

The precision to which the intensity I attenuated by passing through the object 100 is determined depends particularly on the position of said object 100 with respect to the source 32. Therefore, it depends on performances and calibration of the position adjustment means. These aspects will be described in more detail later.

The different transport means 70, 72, 80, 82, 84, 86, 88 and position adjustment means 74, 76, 78, 90, 92, 94, 96, 98 are shown in FIGS. 1 and 2 showing the system as a whole. Their purpose is to transport the object 100 to each apparatus 2, 30 used to determine or adjust the relative position of the object 100 with respect to the elements making up each determination apparatus 2, 30.

A support plate 150 supports components of the general system, namely the apparatus 2 used to determine the significant dimension, the apparatus 30 used to determine the attenuated intensity of the beam, the transport means, the first adjustment means and the second adjustment means. The displacement directions are shown diagrammatically by coordinate system 152 in FIG. 2. Displacements take place in the horizontal plane (X, Y) of the support plate 150, or along the vertical direction Z perpendicular to the horizontal plane (X, Y) of the support plate 150.

The transport means 70, 72 are designed to transport the object 100 into a first position in which the apparatus 2 determines the significant dimension of said object 100. They include a horizontal turntable 70 activated by a stepping motor 72, both installed on the support plate 150. In the example shown, the turntable 70 includes twelve object locations.

The first adjustment means 74, 76, 78 are designed to adjust the position of the object 100 with respect to the two infrared assemblies 4, 6 and 8, 10 that are used to measure the significant dimension x of the object 100.

The adjustment means 74 is a slide oriented along the X direction, along which the base 26 of the infrared radiation apparatus 2 used to determine the dimension, and the turntable 70 are located.

The two infrared assemblies 4, 6 and 8, 10 are installed on the base 26 such that the axes 12, 14 of the infrared beams are parallel to the direction X. For a given set of objects for which the dimensions are substantially all of the same order of magnitude, the relative positions of the base 26 and the turntable 70 along this direction X are preferably fixed once and for all at the beginning of the series of measurements for the given set of objects.

The adjustment means 76 is an actuator, the function of which is to bring the first infrared assembly 4, 6 closer to or further from the second infrared assembly 8, 10 along the Y direction. This displacement of the first infrared assembly 4, 6 along the Y direction provides a means of positioning the object 100 with a precision of about one micron with respect to the two infrared radiation beams to determine its significant dimension X (diameter or thickness).

The adjustment means 78 is an actuator, the function of which is to move the base 26 along the Z direction. The amplitude of this displacement is relatively small, so as to prevent the base 26 from coming out of the slide 74. Displacement of the base along the Z direction provides a means of obtaining the dimension of the object 100 used to determine its significant dimension x, with a precision of about one micron.

The transport means 70, 72, 80, 82, 84, 86, 88 also perform the function of displacing the object 100 from its first position in which the apparatus 2 determines the significant dimension x towards its second position in which the apparatus 30 determines the attenuated intensity I of the photon beam. They include the turntable 70 driven by its stepping motor 72. Several objects 100 are located on a circle on the turntable 70, rotation of said plate 70 performs two simultaneous actions consisting firstly of transporting an object 100 to its first measurement position and secondly moving the previous object 100 from its first measurement position to bring it to an intermediate position after it had performed an angular displacement of an angle A. In the example illustrated in FIGS. 1 and 2, this angle A is 90°. The transport means also include a handling arm 80 that grips the object 100 installed on the turntable 70 in its intermediate position and transports it on an irradiation support 90 located between the collimator 32 of the source and the collimator 40 of the detector. In the example illustrated in FIG. 2, the handling arm 80 comprises a gripping clamp 82 articulated on an intermediate segment 84, itself articulated on an actuator 86 capable of moving in translation along the X direction of the support plate 150, along guide rails 88. Tightening/loosening movements of the clamp 82 and pivoting movement of it about the segment 84, and pivoting movements of the segment 84 with respect to the actuator 86 are controlled by actuators (not shown).

The function of the second adjustment means 90, 92, 94, 96, 98 is to adjust the position of the object 100 with respect to the source 32 and the detector 40 of the gamma spectrometry apparatus 30 to determine the intensity of the beam that will pass through said object 100. They include the irradiation support 90 on which the object 100 is installed. This irradiation support 90 has a top face 92 with a V-shaped cross-section, or any other equivalent means such that the object 100 is automatically installed in a stable equilibrium position on said irradiation support 90, and particularly that it cannot move with respect to the irradiation support 90 along the X direction of the support plate 150. The irradiation support 90 is positioned along the X direction of the support plate 150 by means of a slide 94 that is preferably coincident with the slide 74. For a given set of objects 100, this positioning is done once and for all at the beginning of the series of measurements corresponding to a given set of objects. The irradiation support 90 may be moved along the Y direction of the support plate 150 by means of an actuator 96 and along the Z direction perpendicular to the support plate 150 by means of an actuator 98. The position adjustments made using the actuators 96 and 98 substantially centre the object (along the Z direction) between the slits of the corresponding collimators of the source 32 and the detector 40.

Furthermore, it is necessary to position the object along the Y direction with a precision of about one micron such that the intensity I of the photon beam is measured at exactly the dimension of the object at which its significant dimension x was determined. This positioning is done by bringing the object until it stops on the upper face 92 of the irradiation support 90. For example, it may be brought into contact with this stop by a blowing operation using a blowing device (not shown), that forces compressed air onto the object, along the Y direction, so as to force it into contact with a stop 93 of the irradiation support 90.

FIG. 1 shows connections through appropriate connection means 180 between firstly the different actuators 76, 78, 86, 96, 98 displacing parts free to move in translation and the stepping motor 72 that rotates the turntable 70, and secondly control and steering units 160. These units 160 control the mechanics and automation of the system, and are connected to the system unit 172 of the computer 170 of the acquisition, processing and analysis apparatus 200, by other appropriate connection means 190.

We will now describe the method for determining the density $\rho$ of each object in a given set of objects 100, by comparison with the density $\rho_{emas}$ of one or several objects chosen as standard or reference density, and forming part of the same set of objects 100.

The method is used with algorithms translating series of instructions that automatically perform the different steps in the method.

The method according to the invention includes preliminary calibration steps that are done once and for all before beginning a series of measurements on a given set of objects, and actual determination steps that are done on each object 100 in said set of objects. All steps in the method are shown schematically in FIGS. 9A and 9B.

The calibration steps follow a predetermined chronology and relate to the following components of the system:
step 1: calibration of the position of the two infrared assemblies 4, 6 and 8, 10 of the apparatus 2 for determination of the significant dimension of objects 100,
step 2: calibration of the position of the irradiation support 90 of the gamma spectrometry apparatus 30 for determining the intensity of the photon beam attenuated by crossing through objects 100,
step 3: calibration of the measurement of the source-detector assembly 32, 40 of the apparatus 30.

Figure 10:
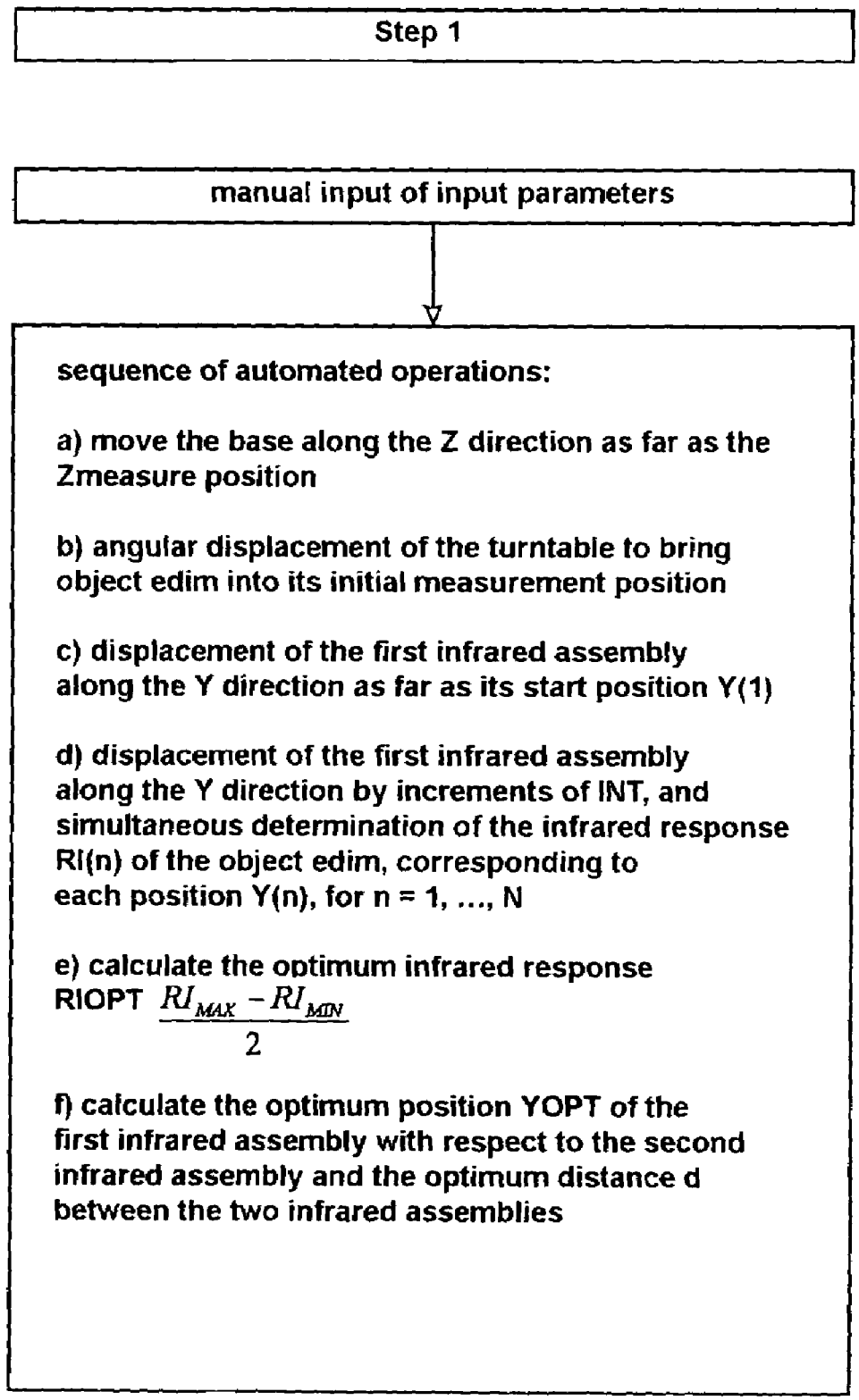
FIG. 10 illustrates the first step in the method that is a step to calibrate the position of the apparatus to determine the significant dimension.

The position calibration step 1 of the two infrared assemblies 4, 6 and 8, 10 is shown in FIG. 10.

This calibration step 1 consists of adjusting the position along the Y direction of the first infrared assembly 4, 6 with respect to the second infrared assembly 8, 10, so as to fix the distance d between the infrared beams emitted by the two emitters 4, 8 respectively, as a function of the precisely known significant dimension $x_{edim}$ of one or several objects with standard dimension edim. In practice, the distance d is determined by progressively moving the first infrared assembly 4, 6 away from the second infrared assembly 8, 10 along the Y direction, the second infrared assembly remaining fixed at a position $Y_{FIX}$, and measuring the infrared response of the object for each position of the first infrared assembly 4, 6.

The position calibration step 1 of the two infrared assemblies 4, 6 and 8, 10 includes firstly operator input of a set of input parameters using an interactive module. These parameters include:
configuration of components that have a micrometric displacement; actuators 76, 78 that manage their dynamics: position, velocity, acceleration,
configuration of the turntable 70, in other words the nature of the objects that occupy the different locations on the turntable 70; arbitrary object 100, or standard dimension object edim, or standard density object emas, or free location,
the position occupied by standard dimension objects edim on the turntable 70, this location being a number varying from 1 to 12 for the example shown,
the position $Z_{measure}$ along the Z direction of the base 26 of the apparatus 2, that corresponds to a dimension $Z_{edim}$ on the object edim with respect to the base of the object,
the positions Y(1) and Y(N) limiting the displacement interval of the first infrared assembly 4, 6 along the Y direction,
the step INT expressed in μm of the displacement of the first infrared assembly 4, 6 along the Y direction $$\left( \frac{Y_{DEP} - Y_{ARR}}{INT} \right.$$

must be an integer number).

The step 1 to calibrate the position of the two infrared assemblies 4, 6 and 8, 10 then includes the following automated operations:

a) displacement of the base 26 along the Z direction as far as the $Z_{measure}$ position by actuation of the actuator 78, b) angular displacement of the turntable 70 so as to transport the standard dimension object edim as far as its initial measurement position with respect to the apparatus 2, c) displacement of the first infrared assembly 4, 6 along the Y direction as far as its start position Y(1) by actuation of the actuator 76, d) progressive displacement of the first infrared assembly 4, 6 along the Y direction in successive increments of INT, moving it away from the second infrared assembly 8, 10 fixed at a position $Y_{FIX}$ between the Y(1) and Y(N) positions, and simultaneously determination of the infrared response RI(n) of the object edim corresponding to each position Y(n) as follows:

d-1) angular displacement of the turntable 70 so as to transport the standard dimension object edim to its final measurement position, d-2) measure the infrared response RI(n) of said standard dimension object edim, d-3) angular displacement of the turntable 70 so as to bring the standard dimension object edim to its initial measurement position, e) calculate the optimum infrared response $$RI_{OPT} = \frac{RI_{MAX} - RI_{MIN}}{2}$$

where: $RI_{MIN}$ is the value of the minimum saturation of the infrared response; at the beginning of the calibration, separation between the two infrared assemblies 4, 6 and 8, 10 is very much less than the significant dimension $x_{edim}$ of the standard dimension object edim; consequently, when 50% of the first infrared beam is intercepted by the object edim, 100% of the second infrared beam is intercepted by this object edim; the first infrared responses then have an identical so-called "saturated" value $RI_{MIN}$, and: $RI_{MAX}$ is the value of the maximum saturation of the infrared response; at the end of the calibration, separation between the two infrared assemblies 4, 6 and 8, 10 is very much greater than the significant dimension $x_{edim}$ of the standard dimension object edim; consequently, when 50% of the first infrared beam is intercepted by the object edim, 0% of the second infrared beam is intercepted by this object edim; the last infrared responses then have an identical so-called "saturated" value $RI_{MAX}$, f) calculate the optimum position $Y_{OPT}$ of the first infrared assembly 4, 6 with respect to the second infrared assembly 8, 10; the optimum infrared response $RI_{OPT}$ is between two previously calculated successive values RI(j) and RI(k) of the infrared response, that correspond to the two positions Y(j) and Y(k) of the first infrared assembly 4, 6 respectively; the optimum position YOPT is deduced from these values as follows:

$$\text{If } \frac{RI_{OPT} - RI(j)}{RI_{OPT} - RI(k)} < 1, \text{ then } Y_{OPT} = Y(j)$$

$$\text{If } \frac{RI_{OPT} - RI(j)}{RI_{OPT} - RI(k)} > 1, \text{ then } Y_{OPT} = Y(k)$$

Operations a) to f) above may be repeated using as many standard dimension objects edim as necessary.

At the end of the step 1 to calibrate the position of the two infrared assemblies 4, 6 and 8, 10, a first calibration file is created that in particular comprises the optimum distance d of the two infrared assemblies 4, 6 and 8, 10 corresponding substantially to the significant dimension of objects $d=\|Y_{FIX}-Y_{OPT}\|$.

Figure 11:
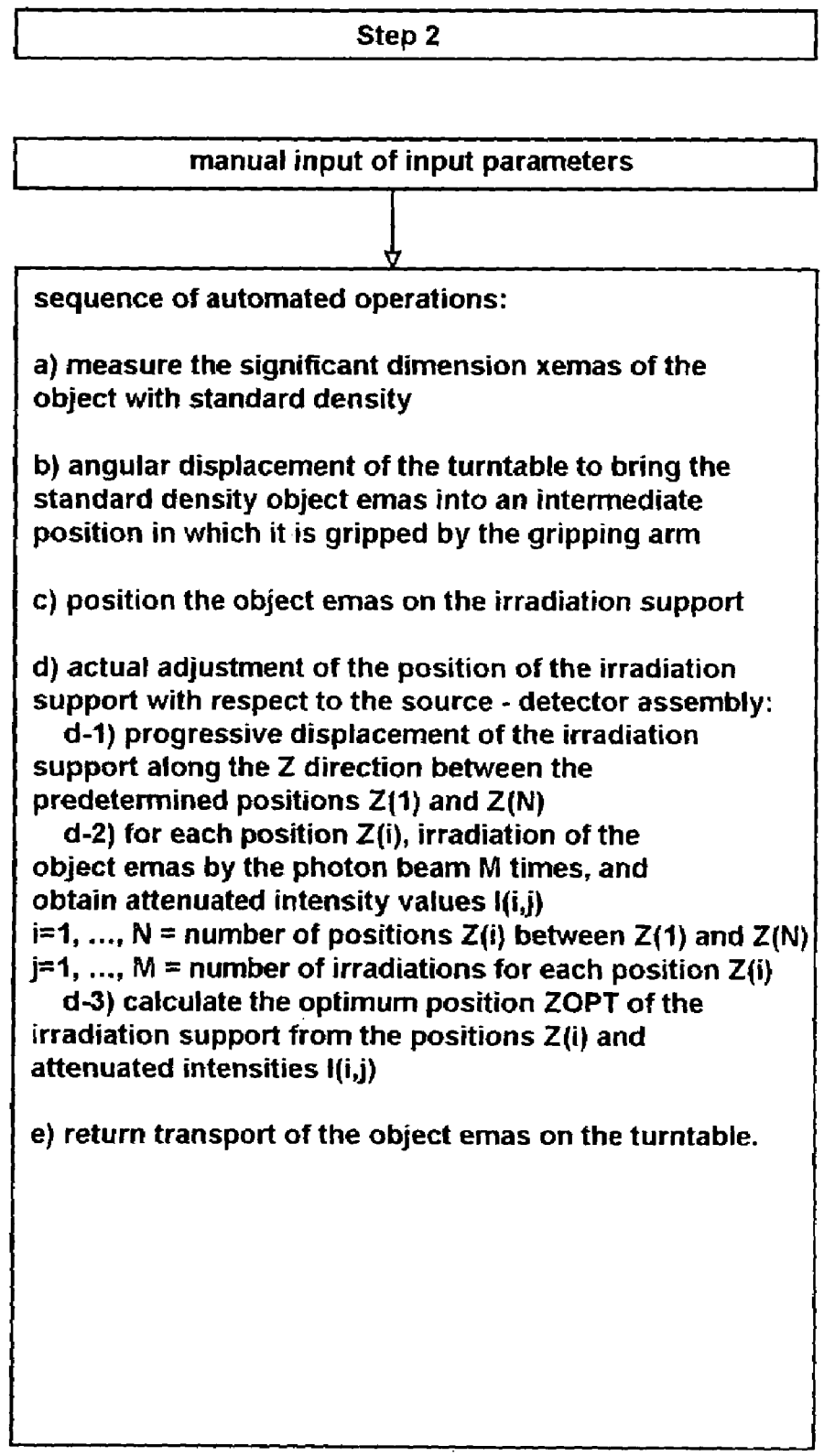
FIG. 11 illustrates the second step of the method that is a step to calibrate the position of the apparatus to determine the attenuated photon intensity.

The position calibration step 2 of the irradiation support 90 of the gamma spectrometry apparatus 30 for determining the intensity of the photon beam attenuated by passing through the objects 100 is illustrated schematically in FIG. 11.

This calibration step 2 consists of adjusting the position along the Z direction of the irradiation support 90 with respect to the source 32 and the associated detector 40, so as to fix the position $Z_{OPT}$ along the Z direction of the top face 92 of the irradiation support 90 on which the objects 100 passed through the photon beam are positioned, as a function of the precisely known density ρ of one or several standard density objects emas. In practice, the position $Z_{OPT}$ is determined by gradually moving the irradiation support 90 along the Z direction and irradiating the standard density object emas installed on the irradiation support 90 several times for each position of this irradiation support. It is determined by calculating a minimum of an order 4 polynomial regression. It includes a step to determine the significant dimension $x_{emas}$ of each standard density object emas.

The step 2 to calibrate the position of the irradiation support 90 of the apparatus 30 comprises firstly a step in which an operator inputs a set of input parameters using an interactive module. These parameters include:

configuration of components that have a micrometric displacement: actuators 96, 98 used to manage their dynamics: position, velocity, acceleration, configuration of the turntable 70, in other words the nature of the objects that occupy the different positions on the turntable 70; arbitrary object 100, or standard dimension object edim, or standard density object emas, or free location, the location occupied by the standard density objects emas on the turntable 70, this position being a number varying from 1 to 12 for the example shown, the measurement duration or count time, the positions Z(1) and Z(N) limiting the displacement interval of the irradiation support 90 along the Z direction, the number M of the measurements of the photon intensity attenuated by passing through the object, for each position Z(i) occupied by the irradiation support, for i=1, . . . , N.

The step 2 to calibrate the position of the irradiation support 90 of the apparatus 30 then includes the following automated operations:

a) determination of the significant dimension $x_{emas}$ of the standard density object, in accordance with step 4 that will be described below, b) angular displacement of the turntable 70 by an angle A, in order to transport the standard density object emas into an intermediate position in which it will be gripped by the gripping arm 80, c) position of the object emas on the irradiation support 90, that comprises the following sub-operations:

c-1) displacement of the irradiation support 90 downwards and along the Z direction by actuation of the actuator 98, c-2) displacement of the handling arm 80 from its waiting position to become vertically in line with the intermediate position of the object emas, by actuation of the actuator 86, c-3) gripping the object emas by the handling arm 80, and then transport of the object until it is vertically in line with the top face 92 of the irradiation support 90, by actuation of the actuator 86, c-4) displacement of the irradiation support 90 as far as the position Z(1), upwards and along the Z direction, by actuation of the actuator 98, c-5) put the object emas down on the top face 92 of the irradiation support 90 using the handling arm 80, by actuation of the actuator 86, c-6) displacement and return of the handling arm 80 as far as its waiting position, by actuation of the actuator 86, c-7) force the object emas into contact with a stop on the top face 92 along the Y direction, for example by a blowing operation that takes place as follows:

displacement of the irradiation support 90 downwards along the Z direction as far as a so-called blowing position in which the object is facing a blowing device provided in the system, send compressed air from the blowing device onto the object emas along the Y direction so as to force it into contact with a stop 93 on the irradiation support 90, d) actual adjustment of the position of the irradiation support 90 with respect to the source 32 and the associated detector 40 that includes the following sub-operations:

d-1) progressive displacement of the irradiation support 90 along the Z direction between the predetermined position Z(1) and the predetermined position Z(N), d-2) for each position Z(i), i=1, . . . , N, irradiation of the standard density object emas by the photon beam a number M of times, which leads to a set of values of attenuated intensity I(i, J), where i=1, . . . N represents the number of successive positions Z(i) occupied by the irradiation support 90 and j=1, . . . , M represents the number of irradiations made at each position Z(i), d-3) calculate the optimum position $Z_{OPT}$ of the irradiation support 90 starting from an order 4 polynomial regression of positions Z(i) with respect to the attenuated intensities I(i, j), this order 4 polynomial regression being predetermined and integrated as a data item of the acquisition, processing and analysis apparatus 200, e) return transport of the object with standard density emas on the turntable 70 using a sequence of operations the same as the sub-operations c-1) to c-6) described above but in the reverse order.

After completion of step 2 to calibrate the position of the irradiation support 90 of the gamma spectrometry apparatus 30 for determining the intensity of the photon beam attenuated by passing through the objects 100, a second calibration file is created that in particular comprises the optimum position $Z_{OPT}$ of the irradiation support 90 along the Z direction.

Step 3 to calibrate the measurement of the gamma spectrometry determination apparatus 30 includes the following automated operations:

a) measurement of the photon intensity $I_{emas}$ attenuated by passing through a standard density object emas used as a reference, b) calculate the attenuation mass coefficient $\mu_m$ of the standard density object, and then of all objects in the set of objects using the following relation:

$$\rho_{emas} = \frac{1}{\mu_m x emas} \cdot L_n \frac{I_{emas}}{I_O}$$

At the end of step 3 to calibrate the measurement of the gamma spectrometry apparatus 30 to determine the intensity of the photon beam attenuated by passing through objects 100, a third calibration file is created that in particular includes the photon intensity $I_{emas}$ attenuated by passing through the standard density object emas.

The actual determination steps also follow a predetermined chronology and concern the following operations:

step 4: determine the significant dimension x of the object 100 to be tested, step 5: transport the object 100 towards the irradiation support 90, step 6: adjust the position of the object 100 by adjusting the position of the irradiation support 90 with respect to the source 32 and the associated detector 40, step 7: determine the attenuated intensity I of the photon beam transmitted through the object 100, step 8: acquisition, processing and analysis of the spectrum obtained, step 9: determination of the relative variation $$\frac{\Delta \rho}{\rho}$$

of the density of the object 100, relative to the density of one or several standard density objects emas, step 10: return transport of the object 100 as far as its location on the turntable 70.

Figure 13:
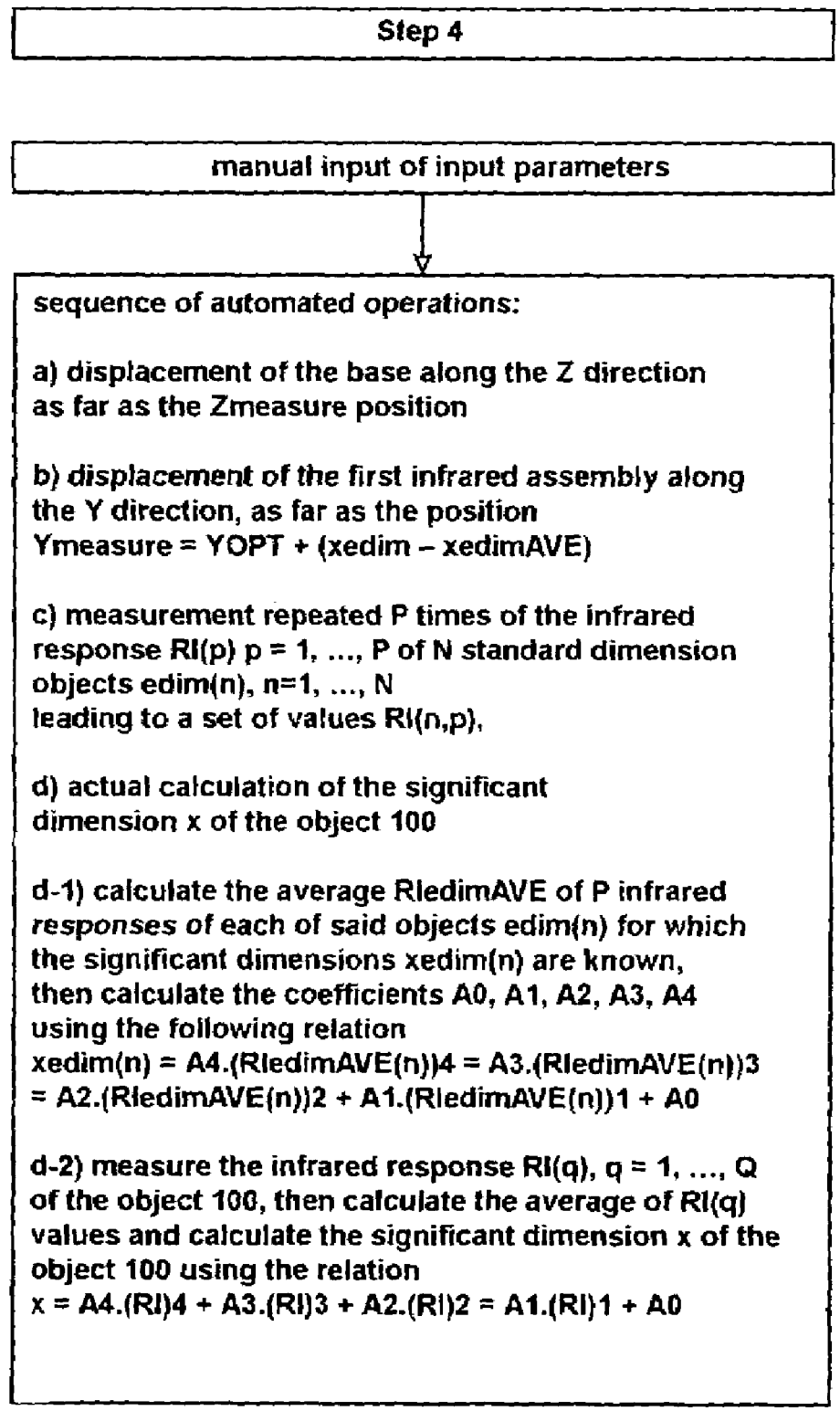
FIG. 13 illustrates the fourth step of the method that is a step to determine the significant dimension of an object.

Step 4 to determine the significant dimension x of the object 100 to be tested is illustrated schematically in FIG. 13. It consists firstly of the operator inputting a set of input parameters using an interactive module. These parameters include:

configuration of components that have a micrometric displacement: actuators 76, 78 used to manage their dynamics: position, velocity acceleration, configuration of the turntable 70, in other words the nature of objects that occupy the different locations on the turntable 70; arbitrary object 100, or standard dimension object edim, or standard density object emas, or free location, the location occupied by the object 100 on the turntable 70, this location being a number varying from 1 to 12 for the example shown, the position $Z_{measure}$ along the Z direction of the base 26 of the apparatus 2, that corresponds to a dimension z on the object 100 with respect to the base of the object, the number P of infrared measurements for each standard dimension object edim(n), n=1, . . . , N, where N is the number of standard dimension objects, the number Q of infrared measurements for the object 100.

Step 4 to determine the significant dimension x of the object 100 to be tested also uses data contained in the first calibration file output from step 1.

The step 4 to determine the significant dimension x of the object 100 to be tested then includes the following automated operations:

a) displacement of the base 26 along the Z direction as far as the position $Z_{measure}$, by actuation of the actuator 78, b) displacement of the first infrared assembly 4, 6 along the Y direction, by actuation of the actuator 76, as far as the position $Y_{measure}$ defined by:

$$Y_{measure} = Y_{OPT} + (X_{edim} - X_{edimAVE})$$

where:

$Y_{OPT}$ is the optimum position obtained in calibration step 1, this value being contained in the first calibration file, $X_{edim}$ is the dimension of the standard dimension object edim used during the calibration step 1, this value being contained in the first calibration file, $X_{edimAVE}$ is the significant average dimension of all standard dimension objects edim, this value being given by the manufacturer, c) measurement of the infrared response RI(p), repeated P times, p=1, . . . , P of N standard dimension objects edim(n), n=1, . . . , N, which leads to a set of values RI(n, p), d) calculation of the significant dimension x of the object 100 as follows:

d-1) calculate the average $$RI_{edimAVE} = \frac{\Sigma RI(n, p)}{P}$$

of the infrared responses of each standard dimension object edim(n) for which the significant dimension $x_{edim}(n)$ is known, and use of an order 4 polynomial regression of the significant dimensions $x_{edim}(n)$ to calculate the coefficients $A_0, A_1, A_2, A_3, A_4$ of a relation of the following type:

$$x_{edim}(n) = A_4 \cdot (RI_{edimAVE}(N))^4 + A_3 \cdot (RI_{edimAvE}(n))^3 + A_2 \cdot (RI_{edimAVE}(n))^2 + A_1 \cdot (RI_{edimAvE}(n))^1 + A_0,$$

d-2) measurement of the infrared response RI(q), repeated Q times, q=1, . . . , Q of the object 100 to be tested, and calculate the average $$RI = \frac{\Sigma RI(q)}{Q}$$

of these infrared responses, and calculate the required significant dimension x of the object 100 by the following relation:

$$x = A_4 \cdot (RI)^4 + A_3 \cdot (RI)^3 + A_2 \cdot (RI)^2 A_1 \cdot (RI)^1 + A_0$$

Step 5 to transport of the object 100 to be tested to the irradiation support is an automated step that repeats the sequence of sub-operations b) and c) of the calibration step 2 described in detail in the above.

Step 6 to adjust the position of the object 100 with respect to the source 32 and the associated detector 40 is an automated step that repeats sub-operation d) of the calibration step 2 described in detail in the above.

Step 7 to determine the photon intensity I of the photon beam attenuated by passing through the object 100 consists of an activity measurement that is then acquired, processed and interpreted in a manner known in itself.

The acquisition, processing and analysis step 8 of the spectrum obtained is an automated step that uses calculation algorithms known in themselves executed by the dedicated software located on the computer 170 of the acquisition, processing and analysis apparatus 200.

Step 9 to determine the relative variation $$\frac{\Delta \rho}{\rho}$$

of the density of the object 100 with respect to the density of one or several standard density object(s) emas is shown in summary in FIG. 14. This is an automated calculation step in which the $$\frac{\Delta \rho}{\rho} = \frac{x_{emas}}{x} \left[ 1 - \frac{L_n \frac{I}{I_{emas}}}{\mu_m \rho_{emas} x_{emas}} \right]$$

equation and the data determined in the above steps are used.

The return transport step 10 of the object 100 on its location on the turntable 70 is an automated step that repeats sub-operation e) in the calibration step 2 described in detail above.

The method that has just been described is implemented using a dedicated software. This software comprises five independent modules and a main interactive menu by which an operator chooses to have one of the five modules executed. The five modules include the following functions:

first module: determine the density of an object that includes the calibration step 3 and steps 4 to 10 to actually determine the density, second module: determine the significant dimension of an object, third module: calibrate the position of the apparatus to determine the significant dimension, fourth module: calibrate the position of the apparatus to determine the attenuated photon intensity, fifth module: management of data files.

EXAMPLE

The system and process described above have been tested.

The source was a $^{133}$Ba source with 10 mCi of activity. The duration of acquisitions was of the order of 20 minutes.

Measurements were made on a set of 7 pellets of uranium oxide ($UO_2$) with the following characteristics: diameter, height and density, as given in table I:

TABLE I

| | Pellet No.: i | | | |
|---|---|---|---|---|
| | 1 | 2 | 3 (standard) | 4 |
| Diameter (mm) | 8.165 | 8.143 | 8.166 | 8.147 |
| Height (mm) | 11.54 | 11.44 | 11.27 | 11.49 |
| Density (g · cm³) | 10.260 ± 0.003 | 10.130 ± 0.003 | 9.900 ± 0.003 | 10.150 ± 0.003 |
| Standard difference (g · cm³) | $1.99 \times 10^{-2}$ | $1.98 \times 10^{-2}$ | $1.96 \times 10^{-2}$ | $1.98 \times 10^{-2}$ |

| | Pellet No.: i | | |
|---|---|---|---|
| | 5 | 6 | 7 |
| Diameter (mm) | 8.123 | 8.117 | 8.169 |
| Height (mm) | 11.29 | 11.54 | 11.59 |
| Density (g · cm³) | 9.950 ± 0.003 | 9.960 ± 0.003 | 10.070 ± 0.003 |
| Standard difference (g · cm³) | $1.95 \times 10^{-2}$ | $1.93 \times 10^{-2}$ | $1.97 \times 10^{-2}$ |

Pellet 3 is used as a standard pellet.

The purpose of the measurements is the precise determination of the relative variation of the density of pellets (1, 2, 4, 5, 6 and 7) with respect to the density of the standard pellet (pellet 3), using the system and process according to the invention. The following relation is applicable:

$$\frac{\Delta\rho}{\rho} = \frac{x}{x_i}\left[1 - \frac{L_n\left(\frac{I_i}{I}\right)}{\mu_m \rho x}\right] - 1$$

The diameters of pellets assumed to be "unknown" are obtained by the step to determine the significant dimension, in this case the pellet diameter, by infrared radiation.

The results of counts obtained by gamma spectrometry for each of the six pellets are shown in table II. There were obtained scrupulously respecting the method chronology as described above.

TABLE II

| PELLET No. | I (in hits) | DIFFERENCES IN DENSITY |
|---|---|---|
| 1 | 974725 ± 1974 | (3.448633 ± 0.017045) × 10$^{-2}$ |
| 2 | 1012550 ± 2012 | (2.286541 ± 0.061460) × 10$^{-2}$ |
| 4 | 1009661 ± 2010 | (2.344449 ± 0.016572) × 10$^{-2}$ |
| 5 | 1063886 ± 2063 | (6.611105 ± 0.132441) × 10$^{-3}$ |
| 6 | 1067853 ± 2067 | (5.941459 ± 0.122442) × 10$^{-3}$ |
| 7 | 1014895 ± 2015 | (1.873675 ± 0.017101) × 10$^{-3}$ |

The standard differences of measured density variations were estimated by an uncertainty propagation calculation. Table III is a table comparing these results with theoretical differences given by the pellet manufacturer.

TABLE III

| | Pellet No. | | |
|---|---|---|---|
| | 1 | 2 | 4 |
| [Δρ/ρ] theoretical | 3.63636 × 10$^{-2}$ ± 2.77 × 10$^{-3}$ | 2.32323 × 10$^{-2}$ ± 2.78 × 10$^{-3}$ | 2.52525 × 10$^{-2}$ ± 2.77 × 10$^{-3}$ |
| [Δρ/ρ] measured | 3.44863 × 10$^{-2}$ ± 1.70 × 10$^{-4}$ | 2.28654 × 10$^{-2}$ ± 1.65 × 10$^{-4}$ | 2.34445 × 10$^{-2}$ ± 1.66 × 10$^{-4}$ |

| | Pellet No. | | |
|---|---|---|---|
| | 5 | 6 | 7 |
| [Δρ/ρ] theoretical | 5.0505 × 10$^{-3}$ ± 2.797 × 10$^{-3}$ | 6.0606 × 10$^{-3}$ ± 2.77 × 10$^{-43}$ | 1.71717 × 10$^{-2}$ ± 2.76 × 10$^{-3}$ |
| [Δρ/ρ] measured | 6.611 × 10$^{-3}$ ± 1.32 × 10$^{-4}$ | 5.9415 × 10$^{-32}$ ± 1.22 × 10$^{-4}$ | 1.8737 × 10$^{-2}$ ± 1.71 × 10$^{-4}$ |

Figure 15:
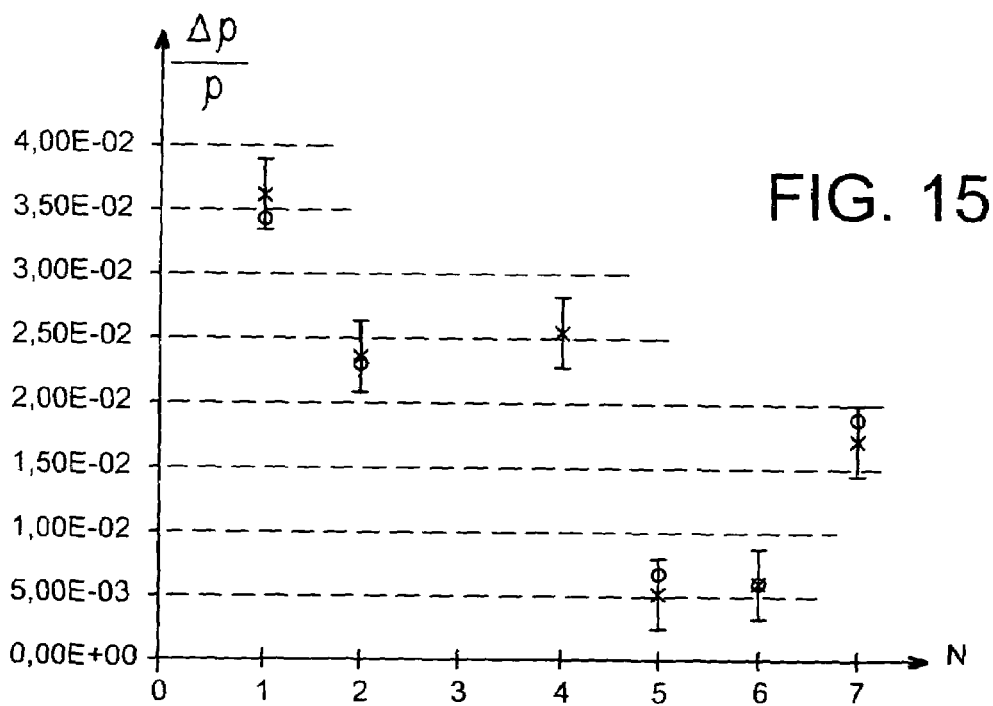
FIG. 15 is a graph showing the relative variation of the density of the objects in a given set of objects relative to the density of one of the standard or reference objects, and compares this relative variation of density obtained by the invention with the relative variation of the theoretical density provided by the objects manufacturer.

These results are illustrated by the chart in FIG. 15. The circles represent the values of $$\frac{\Delta\rho}{\rho}$$

resulting from the measurement, while the crosses represent the values of $$\frac{\Delta\rho}{\rho}$$

given by the manufacturer. The interval materialised represents the standard difference calculated from data supplied by the manufacturer.

These results show that the system and the process according to the invention are capable of detecting a relative variation of the density equal to about 6×10$^{-3}$ with respect to the pellet chosen as the standard object.

The invention claimed is:

1. System for automatic determination of the density of an object (100) belonging to a set of objects, characterized in that it comprises:
    an apparatus (2) to determine a significant dimension (x) of said object (100),
    an apparatus (30) to determine the intensity (I) of a photon beam attenuated by passing through said object (100),
    an acquisition, processing and analysis apparatus (200),
    means (70, 72, 80, 82, 84, 86, 88) of transporting the object (100) to the apparatus (2) for determining its significant dimension (x) and towards the apparatus (30) for determining the attenuated photon intensity,
    first means (74, 76, 78) of adjusting the position of the object (100) relative to the apparatus for determining its significant dimension (x), and
    second means (90, 92, 94, 96, 98) of adjusting the position of the object (100) relative to the apparatus (30) for determining the attenuated photon intensity,
    and in that said first and second adjustment means are capable of moving the object (100) with a precision of the order of one micron with respect to a support plate (150) on which the elements making up the system are installed,
    and in that the position of the object (100) relative to the apparatus (30) for determining the attenuated intensity (I) is adjusted as a function of the significant dimension (x) of said object (100).

2. System set forth in claim 1, characterised in that the acquisition, processing and analysis apparatus (200) includes a computer (170) in which a dedicated software is installed that runs series of instructions and calculation algorithms used in the automatic method for determination of the density of the object (100).

3. System set forth in claim 1, characterised in that the acquisition, processing and analysis apparatus (200) gives the relative variation $$\left(\frac{\Delta\rho}{\rho}\right)$$

of the density (ρ) of the object (100), relative to the known density of at least one standard density object (emas) belonging to the same set of objects (100).

4. System set forth in claim 1 characterised in that the apparatus (2) for determination of the significant dimension of the object (100) includes:
    a first infrared assembly (4, 6) composed of a first infrared emitter (4) and a first infrared receiver (6),
    a second infrared assembly (8, 10) composed of a second infrared emitter (8) and a second infrared receiver (10), the two infrared assemblies (4, 6; 8, 10) being separated from each other by a known distance (d), and emitting infrared beams that are parallel to each other, and the significant dimension (x) of the object (100) is deduced from the infrared response obtained when the object (100) is moved so as to intercept the first infrared beam and the second infrared beam in sequence, along a direction substantially perpendicular to the direction of the axes (12, 14) of the two beams, said infrared response corresponding to the fraction (24) of the second beam not yet intercepted by the object (100) when it is still intercepting half (22) of the first beam.

5. System set forth in claim 4, characterised in that the determination apparatus to determine a significant dimension (2) also includes a third photoelectric transceiver assembly (16, 18) arranged on the input side of the first infrared assembly (4, 6) with respect to the second infrared assembly (8, 10) and intended to make a prior adjustment of the intensity of the two infrared beams.

6. System set forth in claim 4, characterised in that the significant dimension (x) of the object (100) is obtained after moving said object N times and measuring Q infrared responses RI(q), where q is between 1 and Q, with a relation of the following type:

$$x = A_4 \cdot (\text{average } RI(q))^4 + A_3 \cdot (\text{average } RI(q))^3 + A_2 \cdot (\text{average} RI(q))^2 + A_1 \cdot (\text{average } RI(q))^1 + A_0,$$

where $A_0, A_1, A_2, A_3, A_4$, are coefficients obtained previously applying the same relation to at least four objects with standard dimension (edim), for which an infrared response $RI_{(edim)}$ is measured.

7. System set forth in claim 1, characterised in that the apparatus (30) for determining the attenuated intensity of a photon beam is a gamma spectrometry determination apparatus, comprising:
 a source assembly (32) formed from a source and a collimator,
 a detector assembly (40) formed from a detector and a collimator, and
 a gamma photon acquisition and counting system (48).

8. System set forth in claim 7, characterised in that the acquisition and counting system (48) comprises:
 a high-density germanium detector,
 a preamplifier (50),
 a Digital Signal Processor (DSP) (52),
 a high voltage module (54),
 a network module (56),
 a data acquisition computer (170),
 a cryostat (60).

9. System set forth in claim 1, characterised in that the transport means (70, 72, 80, 82, 84, 86, 88) comprise a turntable (70) and a stepping motor (72) driving said turntable (70).

10. System set forth in claim 1, characterised in that the transport means comprise a handling arm (80).

11. System set forth in claim 10, characterised in that the handling arm (80) is an articulated arm equipped with an end clamp (82) intended to grip and put the object (100) down.

12. System set forth in claim 1, characterised in that the first adjustment means comprise:
 a slide (74) to fix the position of a base (26) of the apparatus (2) for determining the significant dimension of the object along a direction X;
 a first actuator (76) to bring the first infrared assembly (4, 6) closer to or further from the second infrared assembly (8, 10) of said apparatus to determine a significant dimension (2) along a Y direction perpendicular to the X direction; and
 a second actuator (78) to move said base (26) of said apparatus to determine a significant dimension (2) along a direction Z perpendicular to the plane (X, Y).

13. System set forth in claim 1, characterised in that the second adjustment means comprise an irradiation support (90) onto which the object (100) is installed between a source (32) and a detector (40) in the apparatus (30) for determining the attenuated intensity of the photon beam passing through the object (100).

14. System set forth in claim 13, characterised in that the second adjustment means comprise:
 a slide (94) to fix an irradiation support (90) along a direction X,
 an actuator (96) to move said irradiation support (90) between a source (32)
 and a detector (40) in the apparatus (30) for determining the attenuated intensity of the photon beam passing through the object (100), along a direction X,
 an actuator (98) to move said irradiation support (90) between a source (32) and a detector (40) in the apparatus (300) for determining the attenuated intensity of the photon beam passing through the object (100), along a direction Z perpendicular to the plane (X, Y).

15. Method for automatically determining the density of an object (100) belonging to a set of objects using a system comprising an apparatus (2) to determine a significant dimension (x) of an object (100) and a gamma spectrometry apparatus (30) to determine the intensity (I) of a photon beam attenuated by passing through an object (100), characterised in that the method includes the following calibration steps:
 a step 1 to calibrate the position of two infrared assemblies (4, 6; 8, 10) in the apparatus (2) to determine the significant dimension (x) of objects in the set of objects which are significant dimension standard objects (edim),
 a step 2 to calibrate the position of an irradiation support (90) of the gamma spectrometry apparatus (30) used to determine the intensity of the photon beam attenuated by passing through the significant dimension (x) of objects in the set of objects which are standard density objects (emas),
 a step 3 to calibrate the measurement of a source-detector (32, 40) assembly of the gamma spectrometry apparatus (30),
 and in that it includes steps to actually determine the significant dimension (x) of the objects (100), that are done on each object (100) in said set of objects.

16. Method set forth in claim 15, characterised in that the calibration step 1 includes operator input of a set of input parameters using an interactive module in which the parameters include:
 configuration of components that have a micrometric displacement including two actuators (76, 78),
 configuration of a turntable (70), in other words the nature of the objects that occupy different locations provided on the turntable,
 the position occupied by each of the significant dimension standard objects (edim) on the turntable (70),
 a position ($Z_{measure}$) along the Z direction of a base (26) of the apparatus to determine a significant dimension (2),
 positions Y(1) and Y(N) limiting a displacement interval of the first infrared assembly (4, 6) along the Y direction,
 a displacement step (INT) of the first infrared assembly (4, 6) along the Y direction.

17. Method set forth in claim 16, characterised in that the calibration step 1 also includes the following operations:
- a) displacement of the base (26) along the Z direction as far as the ($Z_{measure}$) position,
- b) angular displacement of the turntable (70) so as to transport one of the significant dimension standard objects (edim) as far as its initial measurement position with respect to the apparatus to determine a significant dimension (2),
- c) displacement of the first infrared assembly (4, 6) along the Y direction as far as its start position (Y(1)),
- d) progressive displacement of the first infrared assembly (4, 6) along the Y direction in successive increments of (INT), moving it away from the second infrared assembly (8, 10) fixed at a position $Y_{FIX}$ between the Y(1) and Y(N) positions, and simultaneous determination of the infrared response (RI(n)) of said one of the significant dimension standard objects (edim) corresponding to each position (Y(n)):
- e) calculate the optimum infrared response $RI_{OPT}$,
- f) calculate the optimum position $Y_{OPT}$ of the first infrared assembly (4, 6) with respect to the second infrared assembly (8, 10).

18. Method set forth in claim 17, characterised in that the operation d) for progressive displacement includes the following sub-operations:
- d-1) angular displacement of the turntable (70) so as to transport said one of the significant dimension standard objects (edim) to its final measurement position,
- d-2) measure the infrared response (RI(n)) of said one of the significant dimension standard objects (edim),
- d-3) angular displacement of the turntable (70) so as to bring said one of the significant dimension standard objects (edim) to its initial measurement position.

19. Method set forth in claim 17, characterised in that the optimum infrared response $RI_{OPT}$ is obtained using the relation:

$$RI_{OPT} = \frac{RI_{MAX} - RI_{MIN}}{2}$$

where: $RI_{MIN}$ is the value of the minimum saturation of the infrared response,
and: $RI_{MAX}$ is the value of the maximum saturation of the infrared response.

20. Method set forth in claim 19, characterised in that the calibration step 2 includes operator input of a set of input parameters using an interactive module in which the parameters include:
- configuration of components that have a micrometric displacement, including two actuators (96, 98),
- configuration of the turntable (70), in other words the nature of the objects that occupy different locations provided on the turntable,
- the position occupied by each of the standard density objects (emas) on the turntable (70),
- a measurement duration or count time,
- positions Z(1) and Z(N) limiting a displacement interval of an irradiation support (90) along the Z direction,
- a number M of measurements of the photon intensity attenuated by passing through each standard density object, for each position Z(i) occupied by the irradiation support, for i=1, ..., N.

21. Method set forth in claim 20, characterised in that the calibration step 2 also includes the following operations:
- a) determination of a significant dimension ($X_{emas}$) each of the standard density objects (emas),
- b) angular displacement of the turntable (70) by an angle (A), in order to transport said standard density objects (emas) into an intermediate position in which they will be gripped by a gripping arm (80),
- c) positioning of said standard density objects (emas) on an irradiation support (90),
- c-1) displacement of the irradiation support (90) downwards, along the Z direction,
- c-2) displacement of the gripping arm (80) from its waiting position to become vertically in line with the intermediate position of the standard density objects (emas),
- c-3) gripping the standard density objects (emas) by the gripping arm (80), and then transport of the standard density objects (emas) until they are vertically in line with the top face (92) of the irradiation support (90),
- c-4) displacement of the irradiation support (90) as far as the position Z(i), upwards and along the Z direction,
- c-5) put the standard density objects (emas) down on the top face (92) of the irradiation support (90) using the handling arm (80),
- c-6) displacement and return of the handling arm (80) as far as its waiting position,
- c-7) force the standard density objects (emas) into contact with a stop on the top face (92) along the Y direction,
- d) actual adjustment of the position of the irradiation support (90) with respect to a source (32) and an associated detector (40),
- e) return transport of the standard density objects (emas) on the turntable (70) repeating the sequence described in operation c) but in the reverse order.

22. Method set forth in claim 21, characterised in that the operation d) to actually adjust the position of the irradiation support (90) with respect to the source (32) and the associated detector (40) includes the following sub-operations:
- d-1) progressive displacement of the irradiation support (90) along the Z direction between two predetermined positions Z(1) and Z(N),
- d-2) for the positions Z(i), i=1, ..., N, irradiation of the standard density object (emas) by the photon beam a number M of times, which leads to a set of values of attenuated intensity I(i, J), where i=1, ..., N represents the number of successive positions Z(i) occupied by the irradiation support (90) and j=1, ..., M represents the number of irradiations made at each position Z(i),
- d-3) calculate the optimum position ($Z_{OPT}$) of the irradiation support (90) starting from an order 4 polynomial regression of positions Z(i) with respect to the attenuated intensities I(i, j), this order 4 polynomial regression being predetermined and integrated as a data item of an acquisition, processing and analysis apparatus (200).

23. Method set forth in claim 19, characterised in that the step 3 to calibrate the measurement of the gamma spectrometry determination apparatus (30) includes the following automated operations:
- a) measurement of the photon intensity ($I_{emas}$) attenuated by passing through a standard density object (emas),
- b) calculate the attenuation mass coefficient ($\mu m$) of the standard density object, using the following relation:

$$\rho_{emas} = \frac{1}{\mu_m x emas} \cdot L_n \frac{I_{emas}}{I_O}.$$

24. Method set forth in claim 19, characterised in that the actual determination steps also include:
- a step 4 to determine the significant dimension (x) of the object (100) to be tested,
- a step 5 to transport the object (100) towards the irradiation support (90),
- a step 6 to adjust the position of the object (100) by adjusting the position of the irradiation support (90) with respect to a source (32) and an associated detector (40),
- a step 7 to determine the attenuated intensity (I) of the photon beam transmitted through the object (100),
- a step 8 for acquisition, processing and analysis of the spectrum obtained,
- a step 9 to determine the relative variation $$\frac{\Delta \rho}{\rho}$$

of the density ($\rho$) of the object (100), relative to the density of one or several standard density object(s) (emas),
- a step 10 for return transport of the object (100) as far as its location on the turntable (70).

25. Method set forth in claim 24, characterised in that the step 4 to determine the significant dimension (x) of the object (100) to be tested consists of the operator inputting a set of input parameters using an interactive module in which the parameters include:
- configuration of the turntable (70), in other words the nature of objects that occupy the different locations on the turntable,
- the location occupied by the object (100) on the turntable (70),
- a position ($Z_{measure}$) along the Z direction of the base (26) of the apparatus (2),
- a number P of infrared measurements for each standard dimension object (edim(n)), n=1, ..., N, where N is the number of standard dimension objects,
- a number Q of infrared measurements for the object (100).

26. Method set forth in claim 25, characterised in that the step 4 to determine the significant dimension (x) of the object (100) to be tested also includes the following operations:
- a) displacement of a the base (26) in the apparatus (2) along the Z direction as far as the position ($Z_{measure}$),
- b) displacement of a first infrared assembly (4, 6) along the Y direction, as far as a position ($Y_{measure}$) defined by: $Y_{measure}=Y_{OPT}+(X_{edim}-X_{edimAvE})$, where:
- $Y_{OPT}$ is the optimum position obtained in calibration step 1,
- $X_{edim}$ is the dimension of the standard dimension object (edim) used during the calibration step 1,
- $X_{edimAVE}$ is the significant average dimension of all standard dimension objects (edim),
- c) measurement of the infrared response RI(p), repeated P times, p=1, ..., P of N standard dimension objects (edim(n)), n=1, ..., N, which leads to a set of values RI(n, p),
- d) actual calculation of the significant dimension of the object (100).

27. Method set forth in claim 26, characterised in that the operation d) to actually calculate the significant dimension (x) of the object (100) is done as follows:
- d-1) use of an order 4 polynomial regression of the significant dimensions $X_{edim}(n)$ of each of the standard dimension objects (edim), as a function of the average $$RI_{edimAVE} = \frac{\sum RI(n, p)}{P}$$

of infrared responses of said object with standard dimension edim(n), to calculate the coefficients $A_0, A_1, A_2, A_3, A_4$ of a relation of the following type:

$x_{edim}(n)=A^4 \cdot (RI_{edimAVE}(N))^4 + A_3 \cdot (RI_{edimAVE}(n))^3 + A_2 \cdot (RI_{edimAVE}(n))^2 + A_1 \cdot (RI_{edimAVE}(n))^1 + A_0$,

- d-2) measurement of the infrared response RI(q), repeated Q times, q=1, ..., Q of the object 100 to be tested, and calculate the average $$RI = \frac{\sum RI(q)}{Q}$$

of these infrared responses, and calculate the significant dimension (x) of the object (100) by the following relation:

$x=A_4 \cdot (RI)^4 + A_3 \cdot (RI)^3 + A_2 \cdot (RI)^2 + A_1 \cdot (RI)^1 + A_0$.

28. Method set forth in claim 17, characterised in that the operation f) to calculate the optimum position $Y_{OPT}$ is obtained as follows:

If $\frac{RI_{OPT} - RI(j)}{RI_{OPT} - RI(k)} < 1$, then $Y_{OPT} = Y(j)$

If $\frac{RI_{OPT} - RI(j)}{RI_{OPT} - RI(k)} > 1$, then $Y_{OPT} = Y(k)$ where RI(j) and RI(k) are two previously calculated values of the infrared response between which the required optimum response $RI_{OPT}$ lies, that correspond to two positions Y(j) and Y(k) of the first infrared assembly (4, 6) respectively.

29. A method according to claim 15 wherein the objects are nuclear fuel pellets.

30. A method according to claim 29 wherein the method is applied during manufacture of the nuclear fuel pellets.

* * * * *

UNITED STATES PATENT AND TRADEMARK OFFICE
CERTIFICATE OF CORRECTION

| | | |
|---|---|---|
| PATENT NO. | : 7,683,329 B2 | Page 1 of 1 |
| APPLICATION NO. | : 10/594834 | |
| DATED | : March 23, 2010 | |
| INVENTOR(S) | : Abdallah Lyoussi et al. | |

It is certified that error appears in the above-identified patent and that said Letters Patent is hereby corrected as shown below:

Title Page, Item (86) should read

--(86) PCT No.:     PCT/FR2005/000838

§ 371 (c)(1),
(2), (4) Date:    Sep. 28, 2006--.

Signed and Sealed this

Twenty-second Day of June, 2010

David J. Kappos
*Director of the United States Patent and Trademark Office*